United States Patent [19]
George

[11] Patent Number: 6,028,108
[45] Date of Patent: Feb. 22, 2000

[54] PROPOFOL COMPOSITION COMPRISING PENTETATE

[75] Inventor: Mary Mathew George, Maple Shade, N.J.

[73] Assignee: America Home Products Corporation, Madison, N.J.

[21] Appl. No.: 09/176,881

[22] Filed: Oct. 22, 1998

[51] Int. Cl.$^7$ ........................................... A61K 31/05
[52] U.S. Cl. ............................ 514/564; 514/731
[58] Field of Search ...................... 514/564, 731, 514/836

[56] References Cited

U.S. PATENT DOCUMENTS

| | | | |
|---|---|---|---|
| 4,056,635 | 11/1977 | Glen et al. | 424/346 |
| 4,452,817 | 6/1984 | Glen et al. | 424/346 |
| 4,798,846 | 1/1989 | Glen et al. | 514/731 |
| 5,614,170 | 3/1997 | Cacheris et al. | 424/9.365 |
| 5,714,520 | 2/1998 | Jones et al. | 514/731 |

FOREIGN PATENT DOCUMENTS 61-204137  9/1986  Japan .

OTHER PUBLICATIONS

Muller et al., Pharm. Ind. 55(10), 1993, 948–950.
Holzgraefe, M. et al., Clin. Tox 24(3), 1986, 235–244.
Inactive Ingredients Guide, FDA, 1996, 101 (Doc.#139955).
J. Dairy Science, 68, Suppl. 1, 1985, 210.

*Primary Examiner*—Phyllis G. Spivack
*Attorney, Agent, or Firm*—Rebecca R. Barrett

[57] ABSTRACT

A sterile pharmaceutical composition for parenteral administration comprising an oil-in-water emulsion of propofol and an amount of pentetate sufficient to prevent significant growth of microorganisms for at least 24 hours after adventitious extrinsic contamination.

34 Claims, No Drawings

PROPOFOL COMPOSITION COMPRISING PENTETATE

BACKGROUND OF THE INVENTION

The present invention relates to preservative properties of pentetate, particularly the preservative properties of pentetate in an oil-in-water emulsion pharmaceutical composition containing 2,6-diisopropylphenol, i.e. propofol.

Propofol is an injectable anesthetic which can be used to induce and maintain general anesthesia and for sedation, for example, in intensive care units where the duration of treatment may be lengthy. There are a number of known propofol formulations. See, for example, UK 1472793, U.S. Pat. Nos. 4,056,635, 4,452,817, 4,798,846 and 5,714,520.

Propofol formulations have been taught to include preservatives to prevent extrinsic contamination. Ideally, the concentration of preservative is kept to a minimum, especially where the formulation is administered for the maintenance of general anesthesia and sedation where such treatments allow for the possibility of significant amounts of preservative being administered to a patient over the course of treatment. A number of preservatives have been suggested for use in propofol formulations. Oil-in-water formulations present unique requirements which must be satisfied. For instance, for parenteral administration, the preservative must be exerted in the aqueous phase to be effective. However, many ionic species which would exert antimicrobial effects in the aqueous phase tend to destabilize the emulsion. Destabilization of emulsions due to ionic species, and in particular divalent cations, is also known to occur in total parenteral nutrition emulsion systems. Muller et al., *Pharm. Ind.*, Vol 55(10), 948–950 (1993). In addition, to be effective for the intended purpose, namely the prevention of extrinsic contamination, a preservative should be broad spectrum, i.e. effective against gram negative (such as *Pseudomonas aeruginosa* and *Escherichia coli*) and gram positive (*Staphylococcus aureus*) bacteria as well as yeast (such as *Candida albicans*) at useful concentrations. Edetate has been taught to be the only preservative which was broad spectrum and was exerted in the aqueous phase without destabilizing the oil-in-water propofol formulations. See, U.S. Pat. No. 5,714,520.

Pentetate is known as a metal ion chelator. Holzgraefe, M., et al., *Clin. Tox.*, 24(3), 235–244 (1986). It is also listed by the FDA for use in IV infusions. Inactive Ingredients Guide, FDA, pg. 101 (Doc #139955, Jan 1996). Pentetate has been shown to have inhibitory activity against bacteria in brain-heart infusion broth, *J. Dairy Science*, Vol. 68, Suppl. 1, 1985, P210. However, Pentetate has not been previously taught as a preservative useful in oil-in-water emulsions.

It has, thus, surprisingly been found that pentetate not only provides suitable preservative properties in oil-in-water emulsions, but does so without destabilizing the emulsion and at significantly lower concentrations than those necessary for edetate to be an effective preservative.

DESCRIPTION OF INVENTION

The invention is a sterile pharmaceutical composition for parenteral administration comprising an oil-in-water emulsion of propofol and an amount of pentetate sufficient to prevent significant growth of microorganisms for at least 24 hours after adventitious extrinsic contamination.

By an oil-in-water emulsion is meant a distinct two-phase system that is in equilibrium and in effect, as a whole, is kinetically stable and thermodynamically unstable.

Pentetate, as used herein, refers to diethylenetriaminepentaacetate or "DTPA", and derivatives thereof. In general suitable derivatives of DTPA are those salts having lower affinity for DTPA than calcium. Particular derivatives include but are not limited to calcium trisodium pentetate.

Prevention of significant growth of microorganisms is meant growth of microorganism which is preferably no more than a 10 fold increase following extrinsic contamination commonly found in treatment settings such as hospital intensive care units and the like. For purposes of this definition, the contamination is generally about $10–10^3$ colony forming units/ml, at temperatures in the range of 20–25° C.

Typically pentetate is present in compositions of the present invention in amounts sufficient to prevent a 10 fold increase in microbial growth 24 hours after extrinsic contamination. Generally the amount of pentetate is less than 0.3% by weight, the upper limited dictated mainly by the desire to minimize the concentration of preservative used so as to avoid toxicity issues. Preferably, pentetate is present in the range of 0.0005 to 0.005% by weight.

Compositions of the present invention typically comprise from 0.1 to 5% by weight of propofol and more preferably from 1 to 2% propofol. Most preferably, the formulation comprises 1% or 2% propofol.

The oil-in-water emulsion may be prepared by dissolving propofol and other oil-soluble ingredients in a water-immiscible solvent, providing an aqueous phase comprising a surfactant and other water-soluble ingredients (with the exception of pentetate), and homogenizing the oil and aqueous phases to provide a concentrated emulsion.

The water-immiscible solvent is suitably present in an amount that is up to 30% by weight of the composition, more suitably 5–25%, preferably 10–20% and in particular about 10%.

A wide range of water-immiscible solvents can be used in the compositions of the present invention. Typically the water-immiscible solvent is a vegetable oil, for example, soy bean, safflower, cottonseed, corn, sunflower, arachis, castor or olive oil. Preferably the vegetable oil is soy bean oil. Alternatively, the water-immiscible solvent is an ester of a medium or long-chain fatty acid for example a mono-, di-, or triglyceride; or is a chemically modified or manufactured palmitate, a glyceral ester or polyoxyl hydrogenated castor oil. In a further alternative the water-immiscible solvent may be a marine oil, for example cod liver or another fish-derived oil. Suitable solvents also include fractionated oils for example fractionated coconut oil or modified soy bean oil. Furthermore, the compositions of the present invention may comprise a mixture of two or more of the above water-immiscible solvents.

The oil phase, comprising propofol and a water immiscible solvent, is homogenized with an aqueous phase comprising a surfactant to provide a concentrated emulsion. The surfactant may be present in amounts of no more than about 2%, more suitably about 1% to about 2% by weight, and preferably about 1.2% by weight of the composition. Suitable surfactants include synthetic non-ionic surfactants, for example ethoxylated ethers and esters and polypropylene-polyethylene block co-polymers, and phosphatides for example naturally occurring phosphatides such as egg and soya phosphatides and modified or artificially manipulated phosphatides (for example prepared by physical fractionation and/or chromatography), or mixtures thereof. Preferred surfactants are egg and soya phosphatides. Most preferred is egg lecithin. The composition of the present invention is suitably formulated to be at pH 6.5 to 9.5 and more preferably 7.0–8.5, if necessary by means of alkali such as sodium hydroxide.

Tonicity modifier which are compounds which make the composition isotonic with blood, may be added. Tonicity modifiers are suitably present in amounts up to about 3% by weight, more preferably about 1% to about 2.5% and most suitably about 2.25% by weight of the total composition. Suitable tonicity modifiers include glycerin. The concentrated emulsion is brought to final volume with water and again homogenized. The emulsion may be filtered.

Finally, aqueous pentetate is added. Alternatively, pentetate may be added initially in the aqueous phase. The formulation is sterilized.

The composition of the present inventions are typically sterile aqueous formulations and are prepared according to conventional manufacturing techniques using, for example, aseptic manufacture or terminal sterilization by autoclaving.

The compositions of the present invention are useful as anesthetics which includes sedation and induction and maintenance of general anesthesia. Accordingly in another aspect the present invention provides a method of producing anesthesia (including sedation and induction and maintenance of general anesthesia) in a warm-blooded animal, including humans, which comprises administering parenterally a sterile aqueous pharmaceutical composition which comprises an oil-in-water emulsion in which propofol in a water-immiscible solvent is emulsified with water and a surfactant and further comprises an effective amount of pentetate.

Dosage regimes will be appreciated by those skilled in the art and may vary from patient to patient. Generally, dosage levels of propofol for producing general anesthesia are from about 2.0–2.5 mg/kg for an adult. Dosage for maintenance of anesthesia are generally about 4–12 mg/kg/hr. Sedative effects may be achieved with, for example, a dosage of 0.3–4.5 mg/kg/hr.

The advantages referred to above for including pentetate in propofol compositions apply also to intravenous fat emulsions which typically are administered, to patients in need thereof, over periods of a day or more. Examples of such intravenous fat emulsions include Intralipid (marketed by Pharmacia), Lipofundin (Braun) and Travamulsion (Baxter). Intralipid, Lipofundin and Travamulsion are all trademarks. Pentetate used as antimicrobial inhibitor is also extended to all pharmaceutical products and in food and cosmetic industry and to all other chemical industry and natural products that uses preservatives.

This invention provides an intravenous fat emulsion which comprises an amount of pentetate to prevent significant growth of microorganisms for at least 24 hours. In particular the present invention provides a sterile, aqueous composition for parenteral administration which comprises an oil-in-water emulsion in which a water-immiscible solvent is emulsified with water and stabilized by means of a surfactant and which further comprises an amount of pentetate sufficient to prevent significant growth of microorganisms for at least 24 hours.

Suitable therapeutic or pharmaceutical agents are those capable of being administered parenterally in an oil-in-water emulsion. Typically such agents are lipophilic compounds and may for example be antifungal agents, anaesthetics, antibacterial agents, anti-cancer agents, anti-emetics, agents acting on the central nervous system such as diazepam, steroids, barbiturates and vitamin preparations. In particular the present invention relates to such oil-in-water emulsions which typically are administered, to patients in need thereof, over periods of a day or more.

Comments herein relating to typical and preferred propofol compositions of this invention and the preparation thereof apply mutatis mutandis to intravenous fat emulsions, oil-in-water emulsions containing a therapeutic or pharmaceutical agent, food and cosmetic products, orals, topical, and parenteral products.

Dosage levels of propofol for producing general anaesthesia, induction and maintenance, and for producing sedative effect, may be derived from the substantive literature and may be determined by one skilled in the art to suit a given patient and treatment regime.

EXAMPLES

Preparation of Propofol Formulations

TABLE I

| I Components | Quantities % (weight) |
| --- | --- |
| propofol | 1.0 |
| soy bean oil | 10.0 |
| egg lecithin | 1.2 |
| glycerin | 2.25 |
| calcium trisodium pentetate | 0.0005% |
| Sodium hydroxide qs | |
| water for injection to 100 | |

The composition of the present invention is suitably formulated at pH 7.0–8.5.

Preparation:

All processing stages are carried out under nitrogen and weights refer to weight in the final volume.

A sterile aqueous oil-in-water emulsion for parenteral administration is prepared as follows:

1. An aqueous phase is prepared by adding glycerin and egg lecithin in water.
2. The oil phase is prepared by adding propofol to the oil.
3. The oil phase is added to the aqueous phase at 40° C. and homogenized at high pressures greater than 15,000 PSI.
4. The concentrated emulsion is brought to final volume with water and homogenized at high pressure. After the final emulsion is formed, it is filtered and the pentetate aqueous solution is added. Pentetate may be added here or in step 1. It is then filled into containers under nitrogen and autoclaved.

Oil-in-water emulsion containing 0.005%, 0.001% pentetate or 1% propofol and 0.005%, 0.001% or 0.0005% pentetate may be prepared in a similar manner using the quantities of ingredients as described in Table I.

MICROBIOLOGICAL ACTIVITY

Oil-in-water formulations of propofol (Table I) containing various additives and 0%, 0.005%, 0.001% and 0.0005% pentetate were prepared as described above. Broth cultures of four standard USP preservative efficacy test organisms Staphylococcus aureus (ATCC 6538), *Escherichia* coli (ATCC 8739), Pseudomonas aeruginosa (ATCC 9027) and *Candida albicans* (ATCC 1023 1) were added to the test formulations at approximately 100 colony forming units per mL. These aliquots are incubated at 20–25° C. and are tested for viable counts of the said organisms after 24 and 48 hours. Data for the propofol emulsion formulations are given below. Pentetate by itself is effective in preventing a no more than 10-fold increase in growth of micro-organisms for at least 24 hours after microbial contamination at concentrations as low as 0.0005%.

RESULTS

Example 1

Formulation with no preservative

| Organism | Log 10 CFU/mL | |
|---|---|---|
| | Initial | 24 hours |
| S. aureus | 1.8 | 3.1 |
| P. aeruginosa | 1.7 | 3.3 |
| E. coli | 1.8 | >4.8 |
| C. albicans | 1.9 | >4.8 |

Example 2

Formulation with Pentetate (0.005%)

| Organism | Log 10 CFU/mL | |
|---|---|---|
| | Initial | 24 hours |
| S. aureus | 1.9 | 2.0 |
| P. aeruginosa | 1.9 | 0.5 |
| E. coli | 2.0 | 1.8 |
| C. albicans | 2.2 | 2.7 |

Example 3

Formulation with Pentetate (0.001%)

| Organism | Log 10 CFU/mL | |
|---|---|---|
| | Initial | 24 hours |
| S. aureus | 1.9 | 2.0 |
| P. aeruginosa | 1.9 | 0.0 |
| E. coli | 1.9 | 1.7 |
| C. albicans | 2.3 | 2.7 |

Example 4

Formulation with Pentetate (0.0005%)

| Organism | Initial | 24 hours | 48 hours |
|---|---|---|---|
| S. aureus | 1.9 | 2.1 | — |
| S. aureus | 1.9 | 2.2 | 2.6 |
| S. aureus | 2.0 | 2.2 | 2.7 |
| P. aeruginosa | 1.8 | 0.5 | — |
| P. aeruginosa | 2.0 | 0.6 | 0.5 |
| P. aeruginosa | 2.0 | 1.0 | 0.5 |
| E. coli | 1.8 | 1.6 | — |
| E. coli | 2.0 | 1.9 | 1.8 |
| E. coli | 2.0 | 1.9 | 1.5 |
| C. albicans | 2.3 | 2.7 | — |
| C. albicans | 2.0 | 2.3 | 2.4 |
| C. albicans | 2.0 | 2.2 | 2.5 |

Example 5

Fat Emulsion with Pentetate (without Propofol) (0.0005%)

| Organism | Log 10 CFU/mL | |
|---|---|---|
| | Initial | 24 hours |
| S. aureus | 2.1 | 2.7 |
| P. aeruginosa | 2.1 | 1.0 |
| E. coli | 2.0 | 1.7 |
| C. albicans | 2.0 | 2.1 |

COMPARATIVE EXAMPLES

TABLE II

Emulsion Formulation with EDTA

| Components | Quantities % (weight) |
|---|---|
| propofol | 1.0 |
| soy bean oil | 10.0 |
| egg lecithin | 1.2 |
| glycerin | 2.25 |
| disodium edetate | 0.005% |
| Sodium hydroxide qs | |
| water for injection to 100 | |

Oil-in-water formulations of propofol (Table II) containing 0.00125%, 0.0025%, 0.00375% and 0.005% EDTA were prepared as described for the pentetate formulation, except using EDTA in the aqueous phase. The formulations were tested as described above by adding approximately $10^4$, $10^3$, $10^2$ and $10^2$ colony forming units/ml of S. aureus, P.aeruginosa, E.coli, and C.albicans, respectively incubating at 20–25° C. for 24 hours and testing for viable counts of said organisms. Results are shown below. EDTA was found to be ineffective at preventing a no more than 10 fold increase in broad spectrum microbial growth at concentrations of 0.0025% and below.

Comparative Example A

Emulsion Formulation with EDTA (0.00125%)

| Organism | Log 10 CFU/mL | |
|---|---|---|
| | Initial | 24 hours |
| S. aureus | 4.1 | 4.3 |
| P. aeruginosa | 4.0 | 6.3* |
| E. coli | 2.6 | 2.4 |
| C. albicans | 2.8 | 4.2* |

*A more than 10 fold increase in microbial growth was observed.

Comparative Example B

Emulsion Formulation with EDTA (0.0025%)

| Organism | Log 10 CFU/mL | |
|---|---|---|
| | Initial | 24 hours |
| S. aureus | 4.1 | 4.2 |
| P. aeruginosa | 4.0 | 3.7 |
| E. coli | 2.7 | 1.5 |
| C. albicans | 2.8 | 3.9* |

*A more than 10 fold increase in microbial growth was observed.

Comparative Example C

Emulsion Formulation with EDTA (0.00375%)

| Organism | Log 10 CFU/mL | |
|---|---|---|
| | Initial | 24 hours |
| S. aureus | 4.0 | 4.3 |
| P. aeruginosa | 4.0 | 3.7 |
| E. coli | 2.6 | 2.1 |
| C. albicans | 2.9 | 3.8 |

Comparative Example D

Emulsion Formulation with EDTA (0.005%)

| Organism | Log 10 CFU/mL | |
|---|---|---|
| | Initial | 24 hours |
| S. aureus | 4.1 | 4.2 |
| P. aeruginosa | 3.9 | 3.5 |
| E. coli | 2.5 | 2.3 |
| C. albicans | 2.9 | 3.9 |

What is claimed is:

1. A sterile pharmaceutical composition for parenteral administration which comprises an oil-in-water emulsion of a lipophilic pharmaceutical agent and an amount of pentetate sufficient to prevent a no more than 10-fold increase in growth of each of *Pseudoinonas aeruginosa, Escherichia coli, Staphylococcus aureus* and *Candida albicans* for at least 24 hours after adventitious extrinsic contamination.

2. The sterile pharmaceutical composition of claim 1 comprising not more than 30% by weight of a water immiscible solvent.

3. The sterile pharmaceutical composition of claim 1 comprising from 10% to 20% by weight of a water immiscible solvent.

4. The sterile pharmaceutical composition of claim 3 where the water immiscible solvent is a vegetable oil or an ester of a fatty acid.

5. The sterile pharmaceutical composition of claim 4 where the water immiscible solvent is soybean oil.

6. The sterile pharmaceutical composition of claim 1 wherein the pH is about 6.5 to 9.5.

7. The sterile pharmaceutical composition of claim 1 further comprising a surfactant.

8. The sterile pharmaceutical compostion of claim 7 wherein the surfactant is a naturally occurring phosphatide.

9. The sterile pharmaceutical composition of claim 8 wherein the naturally occurring phophatide is egg lecithin.

10. The sterile pharmaceutical composition of claim 7 wherein the surfactant is a non-naturally occurring phosphatide.

11. The sterile pharmaceutical composition of claim 1 which is isotonic with blood.

12. The sterile pharmaceutical composition of claim 11 which is isotonic with blood by incorporation of glycerin.

13. A sterile pharmaceutical composition of claim 1 comprising from about 0.0005% to about 0.1% by weight of pentetate.

14. A sterile pharmaceutical composition for parenteral administration which comprises an oil-in-water emulsion of propofol and an amount of pentetate sufficient to prevent a no more than 10-fold increase in growth of each of *Pseudomonas aeruginosa, Escherichia coli, Staphylococcus aureus* and *Candida albicans* for at least 24 hours after adventitious extrinsic contamination.

15. The sterile pharmaceutical composition of claim 14 comprising 1% to about 2% propofol.

16. The sterile pharmaceutical composition of claim 14 comprising about 1% propofol.

17. The sterile pharmaceutical composition of claim 14 comprising about 2% propofol.

18. A sterile pharmaceutical composition of claim 14 comprising from about 0.0005% to about 0.1% by weight of pentetate.

19. The sterile pharmaceutical composition of claim 14 comprising from 10% to 20% by weight of water immiscible solvent.

20. The sterile pharmaceutical composition of claim 19 where the water immiscible solvent is a vegetable oil or an ester of a fatty acid.

21. The sterile pharmaceutical composition of claim 20 where the water immiscible solvent is soybean oil.

22. The sterile pharmaceutical composition of claim 14 wherein the pH is about 6.5 to 9.5.

23. The sterile pharmaceutical composition of claim 14 further comprising a surfactant.

24. The sterile pharmaceutical composition of claim 23 wherein the surfactant is a naturally occurring phosphatide.

25. The sterile pharmaceutical composition of claim 24 wherein the naturally occurring phosphatide is egg lecithin.

26. The sterile pharmaceutical composition of claim 23 wherein the surfactant is a non-naturally occurring phosphatide.

27. The sterile pharmaceutical composition of claim 14 which is isotonic with blood.

28. The sterile pharmaceutical composition of claim 27 which is isotonic with blood by incorporation of glycerin.

29. A sterile pharmaceutical composition for parenteral administration which comprises an oil-in-water emulsion of propofol and not more than 0.1% by weight of pentetate.

30. A sterile pharmaceutical composition in the form of an oil-in-water emulsion comprising:
   a) about 2% by weight of propofol;
   b) about 10% by weight of soybean oil;
   c) about 1.2% by weight of egg lecithin;
   d about 2.25% by weight of glycerin;
   e) about 0.0005% by weight pentetate;
   f) water to 100%.

31. A sterile pharmaceutical composition in the form of an oil-in-water emulsion comprising:
   a) about 1% by weight of propofol;
   b) about 10% by weight of soybean oil;

c) about 1.2% by weight of egg lecithin;

d) about 2.25% by weight of glycerin;

e) about 0.0005% by weight pentetate;

f) water to 100%.

32. A sterile intravenous fat emulsion comprising an amount of pentetate sufficient to prevent a no more than 10-fold increase in growth of each of *Pseudomonas aeruginosa, Escherichia coli, Staphylococcus aureus* and *Candida albicans* for at least 24 hours after adventitious extrinsic contamination.

33. A sterile intravenous fat emulsion comprising up to about 30% by weight water-immiscible solvent, up to about 2% by weight surfactant, up to about 3% by weight of glycerin and an amount of pentetate sufficient to prevent a no more than 10 fold increase in growth of each of *Pseudomonas aeruginosa, Escherichia coli, Staphylococcus aureus* and *Candida albicans* for at least 24 hours after adventitious extrinsic contamination.

34. A method of limiting microbial growth in a sterile oil-in-water emulsion pharmaceutical composition following extrinsic contamination of said sterile composition comprising incorporating into said oil-in-water emulsion an amount of pentetate sufficient to prevent an at least ten fold increase in the growth of microorganisms for at least twenty-four hours after extrinsic contamination.

* * * * *